United States Patent [19]

Hill et al.

[11] 4,441,363
[45] Apr. 10, 1984

[54] APPARATUS AND METHOD FOR MEASURING CONCENTRATIONS OF SUPERCOOLED LIQUID WATER

[75] Inventors: Geoffrey E. Hill; Duard S. Woffinden, both of Logan; Duane G. Chadwick, North Logan, all of Utah

[73] Assignee: Utah State University Foundation, Logan, Utah

[21] Appl. No.: 281,435

[22] Filed: Jul. 8, 1981

[51] Int. Cl.³ .................. G01W 1/00; G01W 1/08
[52] U.S. Cl. .................. 73/170 R; 340/582; 73/579
[58] Field of Search ............ 73/DIG. 1, 170 R, 579, 73/576, 583, 651, 517 AV; 340/582, 601

[56] References Cited

U.S. PATENT DOCUMENTS

| | | | |
|---|---|---|---|
| 2,283,919 | 5/1942 | Diamond et al. | 73/170 R |
| 3,240,054 | 3/1966 | Roth | 340/582 X |
| 3,483,753 | 12/1969 | Loeb . | |
| 3,626,754 | 12/1971 | Haagen . | |
| 3,779,072 | 12/1973 | Meier . | |
| 3,889,525 | 6/1975 | Bailey | 73/579 |
| 3,967,497 | 7/1976 | Brown . | |
| 4,118,977 | 10/1978 | Olsen et al. . | |

FOREIGN PATENT DOCUMENTS

| | | | |
|---|---|---|---|
| 674497 | 4/1939 | Fed. Rep. of Germany | 340/582 |
| 1006312 | 9/1965 | United Kingdom | 73/DIG. 1 |
| 556358 | 4/1977 | U.S.S.R. | 73/DIG. 1 |

*Primary Examiner*—Charles A. Ruehl
*Attorney, Agent, or Firm*—H. Ross Workman; Rick D. Nydegger; Allen R. Jensen

[57] ABSTRACT

A vibrating wire placed in the humidity duct of a standard radiosonde is used to measure vertical profiles of the concentration of supercooled liquid water in clouds. An electronic circuit is provided for monitoring the natural frequency of vibration which varies according to the mass of ice accumulated on the wire by contact freezing. The time rate of change of ice accumulation is related to the supercooled liquid water concentration. By monitoring the natural frequency, the supercooled liquid water concentration can be found.

20 Claims, 6 Drawing Figures

APPARATUS AND METHOD FOR MEASURING CONCENTRATIONS OF SUPERCOOLED LIQUID WATER

BACKGROUND

1. Field of the Invention

The invention relates to an apparatus and method for measuring meteorological parameters. More particularly, it relates to an apparatus and method for measuring vertical profiles of the concentration of supercooled liquid water.

2. The Prior Art

An intriguing and increasingly more important facet of meteorology is that of weather modification. Of particular interest to meterologists are the processes and techniques surrounding cloud modification so as to induce precipitation. In order to induce precipitation in the atmosphere, nuclei (very small particulates such as dust) must be present on which supercooled liquid water (i.e., water whose temperature is below 0° C. but still exists in the liquid phase) readily condenses and forms an ice crystal. Once the crystal is large enough, it falls as precipitation. Whether this precipitation finally reaches the earth in the form of rain, snow, sleet or hail depends upon air currents, temperature, and humidity.

Many clouds possess the moisture necessary for precipitation, but the temperature of the cloud is too high for ice crystal formation. To induce precipitation, it is common to "seed" the cloud with artificial ice nuclei, such as silver iodide, which have a crystalline structure very much like natural ice. In the presence of silver iodide, the supercooled liquid water molecules behave as if natural ice nuclei were present, thereby catalyzing the formation of precipitation.

It is known in the art that the potential precipitation yield from cloud seeding is related to the supercooled liquid water concentration (hereinafter referred to as "SLW concentration") present in the cloud prior to seeding. Knowledge of SLW concentration is, therefore, an important factor in developing a physical understanding upon which a sound seeding technology can be based and an essential factor in the practical application of weather modification techniques. Moreover, it is believed that SLW concentration measurements may provide significant insights in the study of cloud physics, and may be a sufficiently important indicator of weather patterns as to warrant routine measurement thereof by the U.S. National Weather Service.

Devices, capable of measuring SLW concentrations under certain conditions, are presently found in the prior art. The Johnson-Williams hot wire liquid water content meter, for example, is capable of measuring SLW concentrations at subfreezing temperatures. See C. B. Neal, Jr. and C. P. Steinmetz, "The Calculated and Measured Performance Characteristics of a Heated-Wire Liquid-Water Content Meter for Measuring Icing Severity", *NACA Technical Note* 2615-52. The Johnson-Williams instrument provides a wire exposed to the atmosphere which makes up one of the resistive elements of a balanced wheatstone bridge. Electronic circuitry monitors the cooling effect on the wire as droplets of supercooled liquid water come into contact with the wire, and the SLW concentration can be derived from this cooling effect.

Another device found in the prior art is the Rosemont Ice Detector manufactured by Rosemont, Inc. of Minneapolis, Minnesota. This instrument was developed in response to a need for a reliable aircraft warning system for the detection of icing on the aircraft. The Rosemont device provides a rigid metallic rod that protrudes from the aircraft and vibrates axially at a very high resonant frequency. Supercooled liquid water accumulates on the rod by contact freezing and decreases the frequency of vibration. When the frequency of vibration decreases to a predetermined level, the device activates heating elements within the aircraft and sounds a warning signal.

Although both the Johnson-Williams and Rosemont devices are capable of measuring SLW concentrations, they were designed for use onboard aircraft and, hence, their applications are somewhat limited to the capabilities of aircraft in gathering meteorological data. For example, it is not possible to measure vertical profiles of the SLW concentration (i.e. the concentration of supercooled liquid water as a function of altitude along an essentially vertical path) in an airplane, nor is it advisable to make measurements in close proximity to mountainous terrain or during periods of severe weather conditions. Such measurements, however, are extremely valuable in providing added insight in the study of cloud physics and weather modification. Moreover, the Johnson-Williams and Rosemont devices are relatively expensive and delicate instruments. The result is that much care must be taken in connection with the operation of these instruments.

A very versatile vehicle for acquiring meteorological information, and one that the National Weather Service has used extensively for years is the weather balloon. Not only is the weather balloon ideally suited for use in measuring vertical profiles, it can be used for collecting data over any type of terrain, under any weather conditions. Each year thousands of instrumented weather balloons are released and monitored to gather meteorological information.

It is common for such balloons to carry with them an electronic device called a radiosonde which combines meterorological sensing equipment with a radio transmitter. As a radiosonde equipped balloon ascends into the atmosphere, typically at a rate of approximately 1000 feet per minute, meteorological equipment measures pressure, temperature, and humidity (by use of a barometer, thermistor, and hygrometer, respectively). These data are transmitted to a ground-based receiving station and are recorded. Winds at different levels can be charted from the data obtained from the meteorological sensing equipment and from tracking the balloon.

Since the balloons typically ascend into the atmosphere until they burst, it is not always possible to recover the electronics carried by the balloons. Thus, because of prohibitive costs, it is not economically feasible to simply combine either the Johnson-Williams or the Rosemont device with a standard radiosonde. Indeed, an inexpensive and expendable device for airborne measurements of SLW concentrations is not found in the prior art.

It would, therefore, be an advancement in the art to provide a device for measuring SLW concentrations that is (1) readily integrated into a standard radiosonde or other similar device, (2) inexpensive and therefore expendable, and (3) accurate and reliable in its operation.

BRIEF SUMMARY AND OBJECTS OF THE INVENTION

The present invention is directed to a method and device for measuring supercooled liquid water concentrations. The invention utilizes a vibrating wire which is exposed to the atmosphere. An electronic circuit is provided for vibrating the wire; the frequency of vibration varies according to the mass of ice accumulated on the wire through contact freezing. The SLW concentration is determined by monitoring the change in frequency of the wire. The invention is configurated so as to be readily integrated into a standard balloon-borne radiosonde. Additional electronics are provided for modulating the standard radiosonde transmitter, and for receiving and recording SLW concentration data.

It is, therefore, a primary object of the present invention to provide a balloon-borne instrument for the measurement of vertical profiles of supercooled liquid water concentration.

Another object of the present invention is to provide an instrument for the measurement of SLW concentrations that can be readily integrated into conventional radiosonde systems.

A further object of the present invention is to provide an inexpensive and expendable device for measuring the concentration of supercooled liquid water.

These and other objects and features of the present invention will become more fully apparent from the following description and appended claims taken in conjunction with the accompanying drawings.

DETAILED DESCRIPTION OF THE PREFERRED EMBODIMENT

Reference is now made to the figures wherein like parts are designated with like numerals throughout. The block diagrams of FIGS. 1 and 2 generally illustrate the way in which the various components of the SLW concentration measuring device of the present invention are interconnected. The preferred embodiment of the present invention includes a balloon-borne sensing and transmitting circuit generally illustrated in FIG. 1 and a ground-based receiving and signal processing circuit illustrated in FIG. 2.

Figure 1:
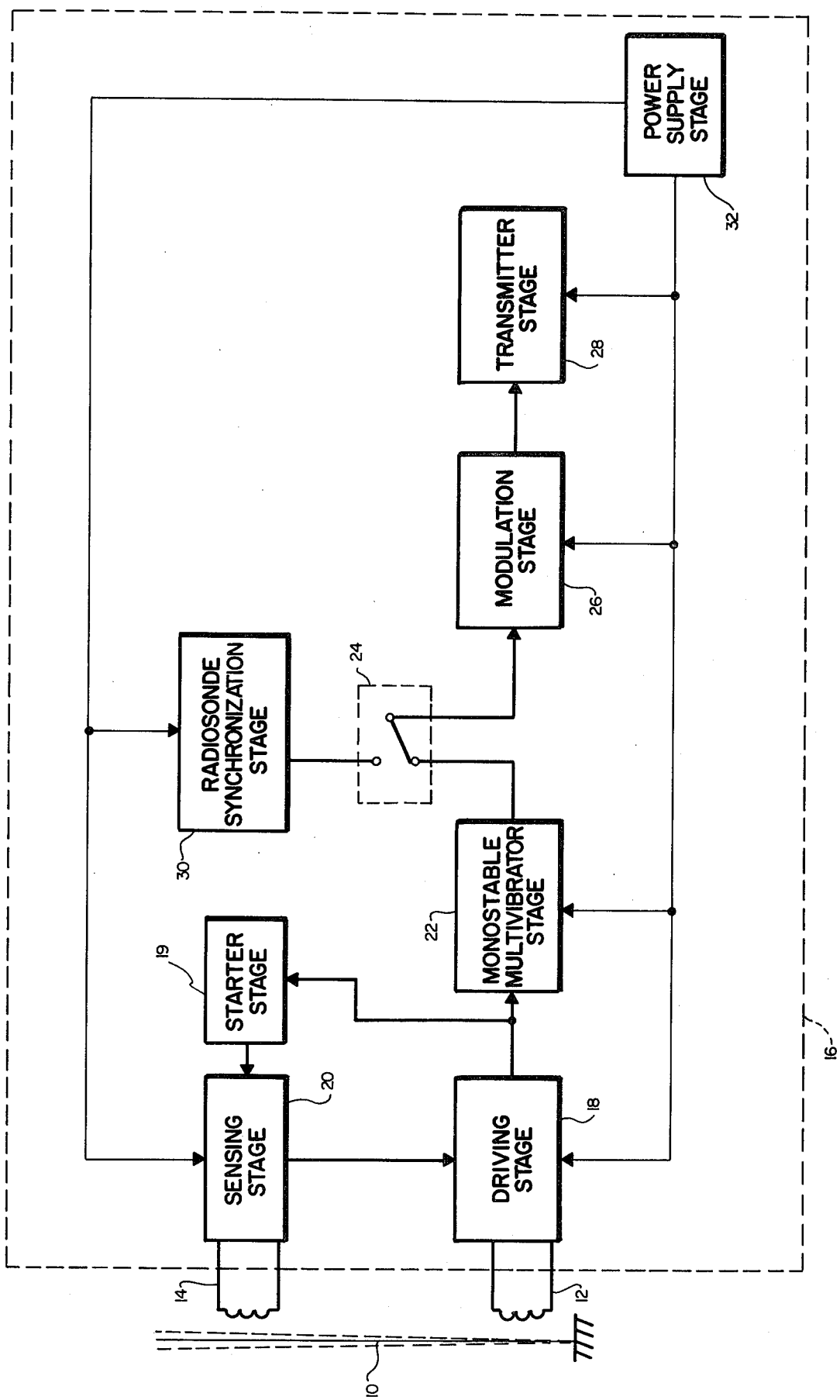
FIG. 1 is a general block diagram of a balloon-borne sensing and transmitting circuit of an embodiment of a supercooled liquid water measuring device within the scope of the present invention.

With particular reference to FIG. 1, the balloon-borne sensing and transmitting circuit basically comprises four components: a vibrating wire 10, a driving coil 12, a sensing coil 14, and an electronic circuit generally designated by the broken line box 16.

Wire 10 is preferably placed in the humidity duct of a standard radiosonde (not shown). A humidity duct is simply a slot or recess on the exterior surface of a radiosonde which is exposed to the atmosphere. The dimensions of wire 10 are chosen so as to obtain a high collection efficiency of supercooled liquid water. See I. Langmuir and K. B. Blodgett, "A Mathematical Investigation of Water Droplet Trajections", *Army-Air Force Technical Report No. 5418* (1946). Generally, the wire should be selected such tht the diameter is as small as possible while, at the same time, the wire should possess sufficient strength and stiffness so as to be capable of sustaining stable transverse vibrations. In the presently preferred embodiment, wire 10 is a piano wire having a diameter of about 0.6 mm and length of about 90 mm. The natural frequency of wire 10 having these dimensions is approximately 53 Hz.

As is schematically illustrated in FIG. 1, wire 10 is fixed at one end to the radiosonde (not shown) and extends approximately 65 mm into the humidity duct such that it is exposed to the atmosphere.

As discussed above, supercooled liquid water possesses the property that it solidifies upon contact with a metallic surface. Accordingly, supercooled liquid water in the atmosphere freezes in the form of ice on the wire. As the ice accumulates on wire 10, the frequency of vibration of the loaded wire (i.e. the combination of wire 10 and the accumulated ice) varies according to the mass of the ice accumulated on wire 10. Since the time rate of ice accumulation on wire 10 is proportional to the concentration of the supercooled liquid water in the atmosphere, the time rate of change in frequency of the loaded wire can be related to the concentration of supercooled liquid water present in the atmosphere.

As the SLW concentration measuring device of the present invention is carried aloft by the radiosonde, it passes through regions where the SLW concentration varies. If the device passes into a region of supercooled liquid water, the supercooled liquid water accumulates on the wire and produces a decrease in the frequency of the loaded wire. The time rate of change of the frequency of the loaded wire is approximately linearly related to the concentration of supercooled liquid water present in the atmosphere.

If, however, the present invention passes into a region where no supercooled liquid water is present, a portion of whatever ice may have already accumulated on the wire may sublimate (depending upon the ambient humidity) and produce an increase in the frequency of the loaded wire.

On rare occasions, such a large amount of ice will accumulate on the wire that the vibration will cause a portion of the ice to crack and break off. Although such break off does affect the frequency of the loaded wire, it does not appreciably affect the instantaneous time rate of change of the vibration of the loaded wire. Thus, the time rate of change of the vibration of the loaded wire provides a continuous measure from which vertical profiles of the SLW concentration (i.e. the concentration of supercooled liquid water as a function of altitude) can be derived.

A solution for the concentration of supercooled liquid water can be obtained through an expression for the frequency of a vibrating wire. An exact expression for the fundamental vibration frequency of a uniform cantilevered wire is $$f = \frac{0.5596}{L^2}\left(\frac{EI^2}{\rho}\right)^{\frac{1}{2}}, \qquad (1)$$

where f is the frequency (Hz), L the wire length (cm), E Young's modulus (dyn cm$^{-2}$), I the moment of inertia (cm), and $\rho$ the density (g cm$^{-3}$). For a piano wire with diamter D=0.06 cm, density 7.7 g cm$^{-3}$), E=20×10$^{11}$ dyn cm$^{-2}$ and L=9.0 cm, the vibration frequency is 52.815 Hz.

Figure 5:
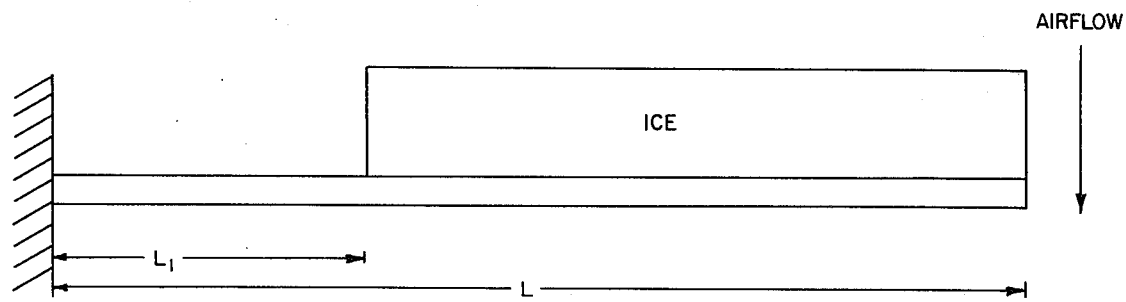
FIG. 5 is a plan view of the composite wire structure.

However, as soon as a portion of the wire becomes loaded with a different material, such as ice, the problem becomes more complex. The configuration of the loaded wire is illustrated in FIG. 5. The length of wire $L_1$ is unloaded and the remaining outer portion of the wire is allowed to accumulate ice with a collecting thickness D, an accumulation thickness $\alpha$D and a length L−$L_1$. To find the vibration frequency under these conditions, we make use of the Rayleigh method, in which the maximum potential energy (PE) is equated with the maximum kinetic energy (KE) during the course of vibration.

The potential and kinetic energies must be integrated over the two wire segments.

Thus, Rayleigh's quotient is written $$\omega^2 = \frac{PE(\max)}{\omega^{-2}KE(\max)} = \frac{\int_0^{L_1}[(E_1I_1)/2](\partial^2y/\partial x^2)^2dx + \int_{L_1}^{L}[(E_2I_2)/2](\partial^2y/\partial x^2)^2dx}{\omega^{-2}\int_0^{L_1}[M_1/2](\partial y/\partial t)^2dx + \omega^{-2}\int_{L_1}^{L}[M_2/2](\partial y/\partial t)^2dx}, \qquad (2)$$

where $\omega=2\pi f$, y is the displacement from a stationary wire, x the distace from the fixed end of the wire, M denotes the mass per unit length, the subscripts 1 and 2 refer to the unloaded and loaded wires, respectively and t is time. An admissible function for the y displacement as a function of x and t is assured as $$y = B[\cos(\pi x/2L) - 1], \qquad (3)$$

where B is some unspecified amplitude.

Figure 6:
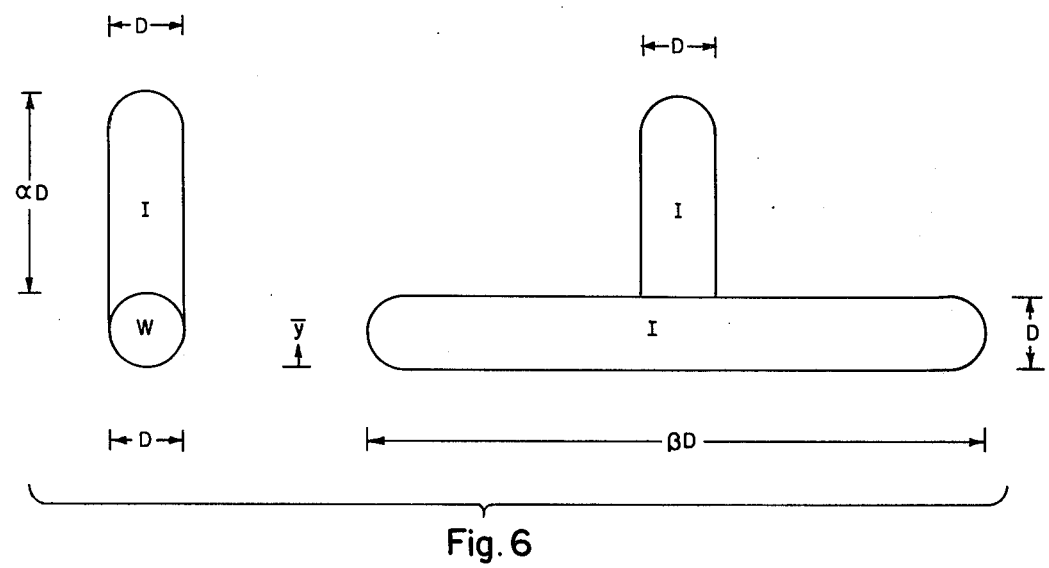
FIG. 6 is a plan view of an equivalent model of the composite wire structure of FIG. 5.

Because the loaded portion of the wire is a composite structure, the steel wire in the loaded portion will be treated as an equivalent ice section as illustrated in FIG. 6. With this assumption, we write $\beta = E_{Steel}/E_{ice}$ and $E_2I_2$ becomes $E_1I_2/\beta$. Integration of (2) yields $$\omega^2 = (\pi^4E_1/32L^4)\frac{(I_1 - I_2/\beta)[L_1/L + (1/\pi)\sin\pi L_1/L] + I_2/\beta}{(M_1 - M_2)[3L_1/2L + (\frac{1}{2}\pi)\sin\pi L_1/L - (4/\pi)\sin\pi L_1/2L] + M_2(3/2 - 4/\pi)}, \qquad (4)$$

where $$I_1 = (\pi/64)D^4, \qquad (5)$$

$$I_2 = (\alpha^3/12)D^4 + \alpha D^2[(\alpha/2+1)D - y]^2 + (\pi/64)\beta D^4 + \beta D^2[y - D/2]^2, \qquad (6)$$

$$y = [\alpha(\alpha/2 + 1) + \beta/2]D/(\alpha + \beta). \qquad (7)$$

In the preferred embodiment, we have $L_1$=2.5 cm, L=9.0 cm, $M_1$=0.2025/9.0=0.0225 g cm$^{-1}$, $M_2=M_1+D^2\rho_i$ where $\rho_i$ is the density of ice, taken here as 0.2 g cm$^{-3}$.

Thus we may compute the vibration frequency for various values of $\alpha$ and $\beta$. ($\alpha$ is the accumulation thickness measured in wire diameters of ice and $\beta$ is the stiffness factor of steel compared to ice.) When $\alpha$=0, we have the equivalent case of a uniform steel wire. For this case Eq. (4) yields a value of f=54.136. This value is higher than the exact solution obtained from (1) by 2.50%, which is to be expected with the Rayleigh approximation. To correct for this difference in result, frequency calculations according to Eq. (4) are multiplied by 0.975.

As a result of extensive research, it has been found that the accumulated ice contributes a negligible amount of added stiffness. The mass of ice is apparently either very soft or laced with tiny cracks. Because of the stiffness of the ice can be assumed negligible, i.e., $\beta\to\infty$, we write (4) accordingly, i.e., $$\omega^2 = (\pi^4E_1/32L^4)\frac{(\pi/64)D^4}{(M_1 - M_2)[3L_1/2L + (\frac{1}{2}\pi)\sin\pi L_1/L - (4/\pi)\sin\pi L_1/2L] + M_2(3/2 - 4/\pi)}. \qquad (8)$$

This result reduces to $$f^2 = \frac{c}{1 + b_1\alpha}, \qquad (9)$$

where in the preferred embodiment c=2930.22 and $b_1$=0.03207 with $\rho_i$=0.2. When (9) is expressed in terms of total mass of ice $m_i$ accumulated by the wire, i.e., (L−$L_1$) times ($M_1-M_2$), we find $$f^2 = \frac{c}{1 + bm_i}, \qquad (10)$$

where c is unchanged and b=6,8528. As before we adjust the approximate solution by a factor of 0.975 so that conformity to the exact solution is obtained. Thus we have $$f^* = f_o(1 = bm_i)^{-\frac{1}{2}}, \qquad (11)$$

where $f_O$=52.78, and from (11) we obtain $$m_i = (f_o^2 - f^{*2})/(bf^{*2}). \qquad (12)$$

The accumulation of ice can be found from (12). The calculation of SLW concentration is $$SLWC = \epsilon^{-1}dm_i/dv, \qquad (13)$$

where $\epsilon$ is the collection efficiency, $dm_i$ the change in ice mass accumulated, and dv the incremental volume swept out by the wire. In turn dv is equal to (L−$L_1$)Dwdt, where w is the air velocity passing the wire and dt the time over which the change in ice mass is found. The result is $$SLWC = [\epsilon(L - L_1)Dw]^{-1}dm_i/dt \qquad (14)$$

and in terms of frequency change, we find with the aid of (12), that $$SLWC = -\{2f_o^2/[\epsilon b(L-L_1)Dwf^{*3}]\}df^*/dt. \quad (15)$$

The air velocity ($\omega$) in the humidity duct of the radiosonde unit has been found to be approximately 96% of the rise rate of the balloon relative to the air.

A small frequency dependence on temperature of the wire has been determined from several soundings made during the absence of clouds. That is, $df^*/dT$ is $-0.0053$ Hz °C.$^{-1}$. This small frequency dependence on temperature can easily be removed prior to the solution of (15).

To monitor the change in the frequency of vibration of the loaded wire, driving coil 12 is positioned in close proximity to the fixed end of wire 10. Driving coil 12 preferably consists of a multi-turn coil of No. 26 AWG wire. It will, of course, be appreciated that other types of electromagnetic coils may be suitably used in the present invention. A time varying current is supplied to coil 12 by electronic circuit 16 which produces a time varying magnetic field in the vicinity of wire 10. The loaded wire is thus forced to undergo transverse vibration by forces resulting from the time varying magnetic field.

Sensing coil 14 is positioned near the free end of wire 10 and preferably consists of a multi-turn coil of No. 39 AWG wire. In accordance with the presently preferred embodiment of the invention, a portion of wire 10 near its free end is magnetized so that the movement of the wire relative to sensing coil 14 induces a time varying current in the sensing coil. The current induced in coil 14 is amplified and fed-back to driving coil 12 by electronic circuit 16.

With further reference to FIG. 1, electronic circuit 16 provides a starter stage 19 that supplies a "starter" current to driving coil 12 through sensing stage 20 and driving stage 18. This starter current is in the form of an alternating current having a frequency of approximately 47 Hz. The frequency of the "starter" current is chosen to be close to the natural frequency of wire 10 (the frequency of the wire before any supercooled water is collected thereon) so that higher order modes of vibration will be inhibited and the fundamental frequency will be enhanced. The range over which the frequency of the starter current may vary depends on the natural frequency of the particular wire chosen.

Once the loaded wire begins to vibrate, a time varying current is induced in sensing coil 14. The frequency of the induced current will be approximately the same as the frequency of the loaded wire since the loaded wire will vibrate at its own characteristic frequency regardless of the frequency of the starter current. The induced current is amplified by sensing stage 20 which, in turn, feeds the amplified signal back to driving stage 18. Once the amplified signal from driving stage 18 reaches a predetermined threshold value, driving stage 18 effectively disables the starter current from starter stage 19 and passes the amplified current from sensing stage 20 to driving coil 12 through driving stage 18. Thus, electronic circuit 16 adjusts the frequency of the current supplied to driving coil 12 such that driving coil 12 reinforces the characteristic frequency of vibration of the loaded wire.

The current signal supplied to driving coil 12 is also coupled to a monostable multivibrator stage 22 which produces a periodic square wave signal having a frequency that duplicates the characteristic frequency of the loaded wire. The output of multivibrator stage 22 is coupled through solid state switch 24 to modulation stage 26 and transmitter stage 28 for frequency modulation and transmission, respectively.

Solid state switch 24 is provided so as to synchronize the SLW concentration data with standard radiosonde data. In the preferred embodiment, radiosonde data (temperature, pressure and relative humidity) are collected, processed, and recorded independently from the SLW concentration data. In order for the SLW concentration data to be studied along with standard radiosonde data, solid state switch 24 passes a short pulse generated by radiosonde synchronization stage 30 each time the radiosonde transmits humidity data thereby providing real time synchronization between the radiosonde data and the SLW concentration data.

Direct current power for each of the active elements in the various stages 18–28 of circuit 16 is proivded by power supply stage 32. Typically, stage 32 consists of a DC battery pack, but it will be appreciated that stage 32 could also comprise photovoltaic cells so as to supplement the battery pack by utilizing solar power.

Figure 2:
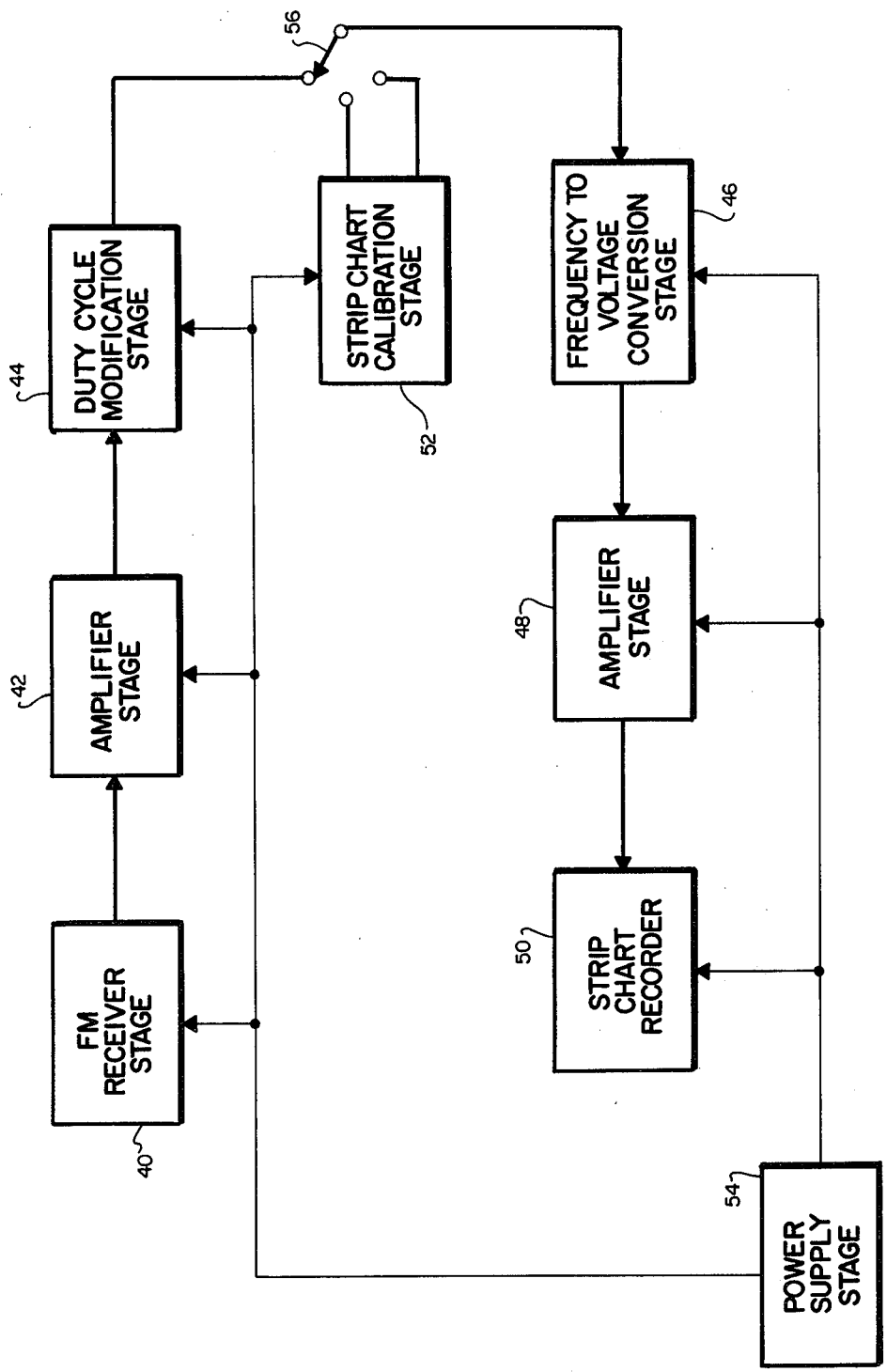
FIG. 2 is a general block diagram of a ground-based receiving and signal processing circuit of an embodiment of a supercooled liquid water measuring device within the scope of the present invention.

The signal transmitted from the balloon-borne sensing and transmitting circuit discussed above is received and recorded by the ground-based receiving and signal processing circuit generally illustrated in FIG. 2. FM receiver stage 40 picks up and demodulates the transmitted signal. Thus, the signal at the output of stage 40 is essentially identical to the output of monostable multivibrator stage 22, and is a periodic square wave signal having a frequency that duplicates the detected characteristic frequency of the loaded wire.

The output of stage 40 is coupled to amplifier stage 42 where the signal is amplified to the required input level of the frequency to voltage ("F/V") conversion stage 46. The output of amplifier stage 42 is coupled to duty cycle modification stage 44 which is coupled through calibration switch 56 to F/V conversion stage 46.

The periodic signal at the input of stage 44 generally consists of a train of pulses having a very narrow pulse width and, thus, a relatively small duty cycle (typically much less than 20%). For accurate frequency to voltage conversion, F/V conversion stage 46 requires at least a 20% duty cycle. Duty cycle modification stage 44 is therefore provided to increase the duty cycle to anywhere from approximately 45% to approximately 55% by effectively spreading the signal pulse width without affecting the signal frequency.

The modified signal is then converted by F/V conversion stage 46 from a periodic, frequency signal to a continuous signal in the form of a DC voltage that is proportional to the frequency of the periodic signal on the input of stage 46. The output of stage 46 is coupled through a second amplifier stage 48 to a strip chart recorder 50. Stage 48 amplifies the continuous output signal from F/V conversion stage 46 to the level required for input into the strip chart recorder 50.

Strip chart calibration stage 52 provides a pair of calibration signals of constant frequency so that the detected and recorded frequency can be referenced to a pair of known frequencies. As a matter of experimental measurements, it has been determined that, for the presently preferred embodiment, the frequencies of 48 and 54 Hz represent the practical limits between which the frequency of vibration of the loaded wire typically ranges. It will of course be apparent that these limits are dependent upon the dimensions of the particular wire chosen. In the presently preferred embodiment, either a 48 Hz or a 54 Hz signal can be selectively coupled to the F/V conversion stage 46, thereby producing reference traces on recorder 50 by a manually operating calibration switch 56.

Alternatively, the output of amplifier stage 48 could be coupled to a computer (not shown) through an analog to digital ("A/D") converter (not shown). With the equation discussed above stored in the computer, the SLW concentration could be directly obtained from an iterative computer solution.

DC power for each of the active elements in the various stages 40–52 is supplied from a power supply 54 which derives its power from conventional AC line source. It will of course be apparent that conventional batteries could also be used to provide the required DC power for stages 40–52.

From the foregoing it will be readily apparent that the SLW concentration measuring device and method represent a significant advancement in the art. The measuring device of the present invention is extremely versatile in that it is sufficiently small and lightweight so as to be readily integrated into conventional radiosonde systems. Moreover, the present invention is relatively inexpensive such that it is economically feasible to utilize it in an expendable balloon-borne radiosonde system.

Figure 3:
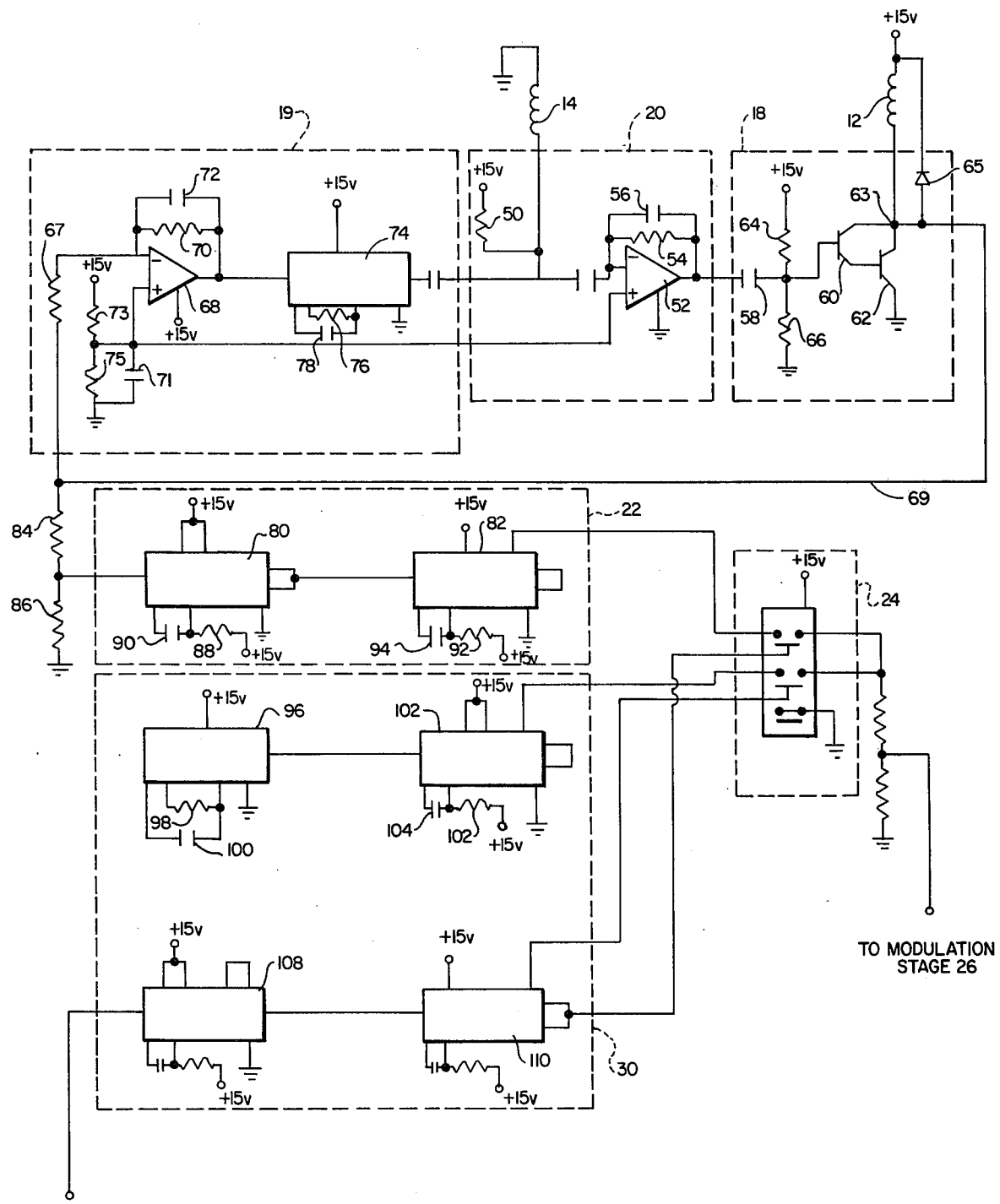
FIG. 3 is a schematic diagram of one embodiment of a sensing and transmitting circuit in accordance with the block diagram of FIG. 1.
Figure 4:
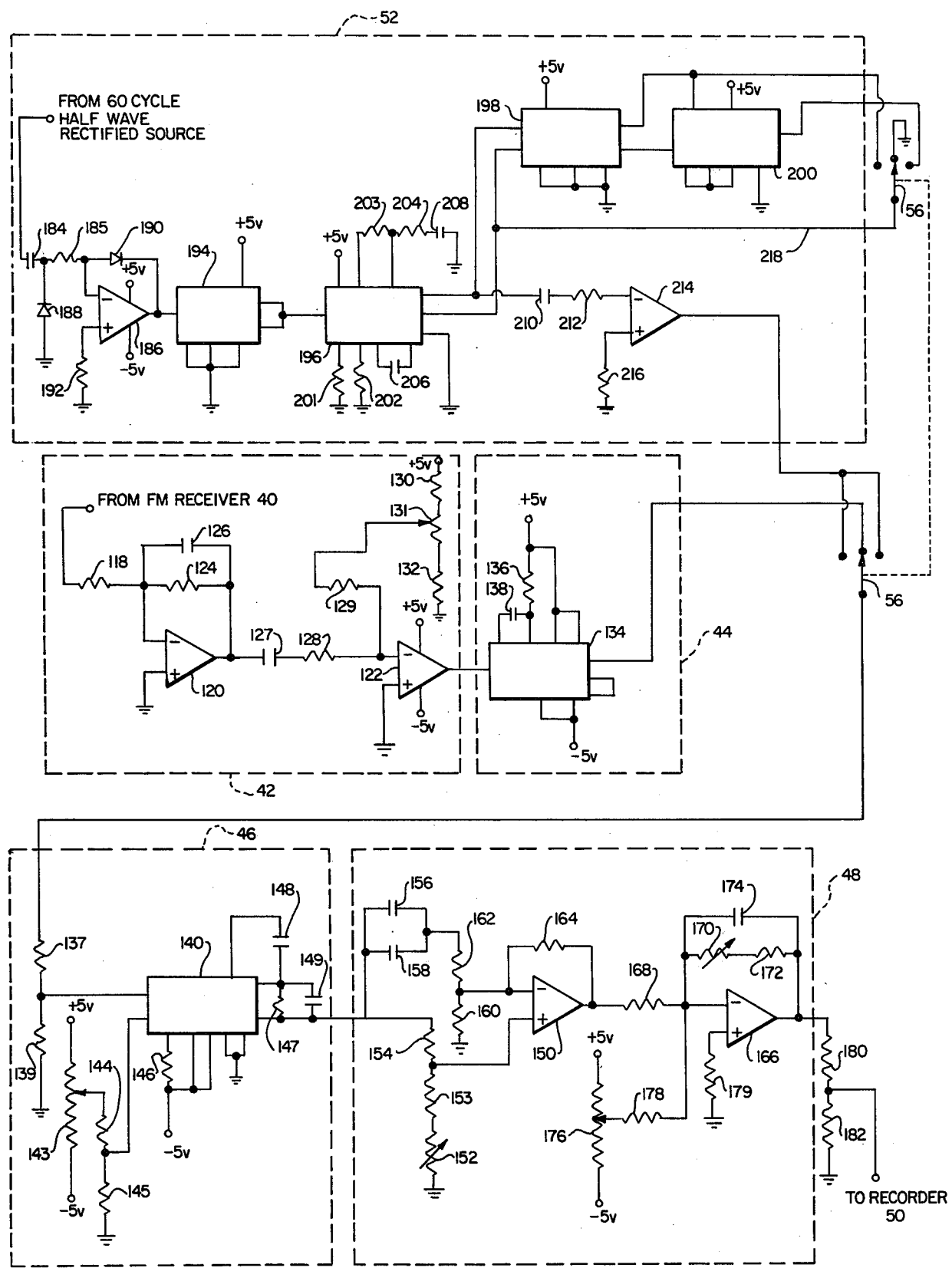
FIG. 4 is a schematic diagram of one embodiment of a receiving and signal processing circuit in accordance with the block diagram of FIG. 2.

Reference is next made to FIGS. 3 and 4, which illustrate in more detail one preferred embodiment for the schematic diagram derived from the block diagrams of FIGS. 1 and 2. Those of ordinary skill in the art will appreciate that various modifications to the detailed schematic diagram of FIGS. 3 and 4 may be easily made without departing from the essential characteristics of the invention as described in connection with the block diagrams of FIGS. 1 and 2. Thus, the following description of the schematic diagram of FIGS. 3 and 4 is intended only as an example of one presently preferred embodiment of a schematic diagram that is consistent with the foregoing description of FIGS. 1 and 2 and the invention as claimed herein.

Driving coil 12 and sensing coil 14 are positioned, as schematically illustrated in FIG. 1, in close proximity to the fixed and free ends of wire 10, respectively. Referring to FIG. 3, movement of wire 10 relative to sensing coil 14 induces a time varying current in sensing coil 14 since a portion of wire 10 is magnetized and movement of the wire relative to coil 14 produces a time varying magnetic field around coil 14. Alternatively, a small DC bias current can be supplied to sensing coil 14 through 2.7k ohm resistor 50 such that movement of the wire causes a fluctuation in the current in coil 14. The current induced in coil 14 is coupled to a low pass filter consisting of operational amplifier (herein referred to as "op amp") 52 which has a frequency response determined by the RC time constant of resistor 54 and capacitor 56. Resistor 54 has a value of 62k ohms and capacitor 56 has a value of 0.047 microfarads such that the upper cutoff frequency of op amp 52 is approximately 54 Hz.

The output of op amp 52 is coupled through a 5 microfarad coupling capacitor 58 to driving stage 18 where it is amplified by a high gain Darlington amplifier consisting of transistors 60 and 62. Transistor 60 may be a TIS98 and transistor 62 may be a TIP33A, both manufactured by Texas Instruments. Resistors 64 and 66 bias the transistors 60 and 62 so as to operate as a class B amplifier. In the illustrated embodiment, resistor 64 is 68k ohms and resistor 66 is 100k ohms.

Driving coil 12 is coupled to output 63 of the Darlington amplifier. Transistors 60 and 62 provide a time varying current to driving coil 12 which produces a time varying magnetic field around wire 10. Diode 65 is preferably coupled in parallel with coil 12 to protect transistors 60 and 62 from inductive feedback.

Under most conditions, transient signals will supply coil 12 with sufficient current to vibrate wire 10 when the power is first supplied to the active elements of the circuit. Wire 10 will vibrate at its characteristic frequency regardless of the frequency of the transient signals. Accordingly, vibration of wire 10 will induce a time varying current in coil 14 having a frequency that duplicates the characteristic frequency of wire 10 plus whatever mass of ice may be accumulated on wire 10. As discussed above, the induced current is filtered, amplified and coupled to driving coil 12 in order to initiate the vibration of wire 10. Hence, wire 10 is driven at its own characteristic frequency by driving coil 12, and any change in the characteristic frequence of vibration is immediately detected and passed to driving coil 12 by sensing stage 20.

It is possible, however, that wire 10 may not begin to vibrate as a result of the transient signals. To automatically initiate vibration of wire 10, starter stage 19 monitors the signal at the output 63 of the Darlington amplifier. The signal from output 63 appears on line 69 from whence it is coupled through 10k ohm resistor 67 to op amp 68 which is wired as a low pass, smoothing filter. The frequency response of op amp 68 is determined by the RC time constant of resistor 70 and capacitor 72. Resistor 70 preferably has a value of 10k ohms and capacitor 72 has a value of 47 microfarads.

Op amps 52 and 68 may be Texas Instruments TL082 integrated circuits. The non-inverting inputs of op amps 52 and 68 are coupled to ground through capacitor 71 and through the voltage divider of resistors 73 and 75. Resistors 73 and 75 provide a DC level shift so that the op amps can be operated off of a single polarity power supply, and capacitor 71 filters out any noise that might be riding on the DC signal. In the preferred embodiment, resistors 73 and 75 are each 10k ohms and capacitor 71 is 47 microfarads.

The output of op amp 68 is coupled to an astable multivibrator 74 which produces a square wave output whenever the signal from op amp 68 is at a high level (i.e., a positive voltage of approximately 11 volts or greater). The frequency of the signal on the output of multivibrator 74 is controlled by the RC time constant of resistor 76 and capacitor 78. Resistor 76 has a value of 47k ohms and capacitor 78 has a value of 0.1 microfarads such that the frequency of the output of multivibrator 74 is approximately 47 Hz.

. If wire 10 does not vibrate, current is not induced in sensing coil 14 and the output 63 of the Darlington amplifier is at ground potential (i.e., 0 volts). Since line 69 is coupled to the inverting input of op amp 68, an input of zero volts to op amp 68 will result in a high level output which will enable multivibrator 74. The output of multivibrator 74 is coupled to sensing stage 20 and is filtered, amplified and coupled to the driving coil as discussed above. Thus, multivibrator 74 supplies an alternating current to driving coil 12 in order to initiate vibration of the wire.

As soon as wire 10 begins to vibrate, however, a current will be induced in coil 14, and output 63 of the Darlington amplifier will no longer be at ground potential. The output of the Darlington amplifier is fed-back to op amp 68 via line 69, causing op amp 68 to switch to a low level (i.e., approximately 4 volts or less), thereby disabling multivibrator 74.

The output of driving stage 18 is also coupled to a pair of bistable multivibrators 80 and 82 through line 69. Resistors 84 and 86 provide a voltage divider to scale the voltage level from driving stage 18 down for input into multivibrator stage 22. In the preferred embodiment, resistors 84 and 86 have values of 47k ohms and 160k ohms, respectively. Multivibrator 80 effectively squares up the signal coming from the Darlington amplifier and has a relatively large duty cycle so as to filter out any transients or "gliches" in the signal at its input. The output of multivibrator 80 is a square wave whose pulse width is determined by resistor 88 and capacitor 90. The values of resistors 88 and capacitor 90 are preferably 2.4 mega ohms and 0.0027 microfarads, respectively.

The output of multivibrator 80 is coupled to the input of multivibrator 82 which modifies the signal pulse width in preparation for frequency modulation. For effective frequency modulation, it is preferable that the pulse width of the signal to be modulated be relatively small. The pulse width of multivibrator 82 is determined by resistor 92 and capacitor 94. The values of resistor 92 and capacitor 94 are preferably 330k ohms and 0.0054 microfarads, respectively. The output of multivibrator 82 is coupled through solid stage switch 24 to modulation stage 26.

As discussed above, radiosonde synchronization stage 30 provides real time synchronization between SLW concentration data and standard radiosonde data. Astable multivibrator 96 outputs square wave which has a frequency controlled by the RC time constant of resistor 98 and capacitor 100. Resistor 98 has a value of 91k ohms and capacitor 100 has a value of 0.047 microfarads such that the frequency of the square wave output of multivibrator 96 is approximately 57 Hz. The output of multivibrator 96 is coupled to multivibrator 102 which narrows the pulse width of the incoming signal prior to frequency modulation. The pulse width of the output of multivibrator 102 is determined by resistor 104 and capacitor 106 which preferably have values of 33k ohms and 0.0027 microfarads, respectively. The output of multivibrator 102 is coupled to solid state switch 24.

Since both the multivibrator stage 22 and the radiosonde synchronization stage 30 supply input signals to modulation stage 26 at various times so as to supply real time synchronization of the data, it is necessary to control the switching of solid state switch 24 so that the proper signal is timely coupled to modulation stage 26. This control is accomplished by applying a control signal to the solid state switch 24 which is derived from the baroswitch (not shown) of the radiosonde (not shown). The humidity contact of the baroswitch is coupled to the input of a pair of multivibrators 108 and 110 which control relay 24. Whenever the radiosonde is collecting humidity data, the baroswitch passes a signal through a humidity contact which causes multivibrators 108 and 110 to drive solid state switch 24 such that the output of multivibrator 102 is coupled to the modulation and transmitter stages. If, however, the radiosonde is monitoring pressure or temperature, multivibrators 108 and 110 will drive solid state switch 24 such that the output of multivibrator stage 22 is coupled to the modulation and transmitter stages.

The output of solid state switch 24 is coupled through the voltage divider of resistor 112 and 114 which preferably have values of 10k ohms and 18k ohms, respectively. Resistors 112 and 114 divide down the voltage from solid state switch 24 to a level suitable for frequency modulation.

Modulation stage 26 and transmitter stage 28 consist of conventional and well-known circuits for frequency modulation and transmission of an FM signal, respectively, and will, therefore, not be described in detail herein. Power for each of the active devices described above is supplied by power supply stage 32 which includes a battery pack which supplies +15 Vdc.

Referring to FIG. 4, the FM signal transmitted by the sensing and transmitting circuit described above is received and demodulated by FM receiver stage 40. FM receiver stage 40 includes conventional and well-known circuits for receiving and demodulating an FM signal and will, therefore, not be described in detail herein. The signal at the output of FM receiving stage is essentially the same as the output from monostable multivibrator stage 22. Moreover, the signal on the output of FM receiver stage 40 duplicates the characteristic frequency of the vibrating wire as detected by sensing coil 14.

The output of FM receiver stage 40 is coupled through 18.2k ohm resistor 118 to amplifier stage 42 which includes a pair of op amps 120 and 122. Op amp 120 is wired so as to provide a low pass filter whose frequency response is determined by resistor 124 and capacitor 126 for smoothing out and removing some of the noise carried on the signal from FM receiver stage 40. The output of op amp 120 is coupled through 22k ohm resistor 128 and 8 microfarad coupling capacitor 127 to op amp 122 which is in a high gain configuration. The gain of op amp 122 is approximately equal to its open loop gain, and resistors 128–132 provide the necessary DC offset so that the output of op amp 122 will be clamped between ground potential and plus five volts. Resistor 131 is a 15k ohm potentiometer and the values of resistors 129, 130 and 132 are preferably 110k ohms, 26k ohms, and 10k ohms, respectively.

The output of op amp 122 is coupled to duty cycle modification stage 44, which consists of a monostable multivibrator 134 for effectively spreading the signal pulse width such that the duty cycle of the signal on the output of multivibrator 134 is between 45% and 55%. The pulse width at the output of multivibrator 134 is determined by resistor 136 and capacitor 138 which preferably have values of 1.5 M ohms and 0.015 microfarads, respectively.

The output of multivibrator 134 is coupled through calibration switch 56 and the voltage divider of resistors 137 and 139 to frequency to voltage ("F/V") conversion stage 46. Resistors 137 and 139 each preferably have a value of 4.7k ohms and serve to scale down the voltage from calibration switch 56 for F/V converstion by F/V converter 140. F/V converter may be a Teledynamics 9401 Frequency to Voltage Converter integrated circuit. Resistors 142–146 and capacitors 148 and 149 are provided as specified by the Teledynamics application manual to enable F/V converter 140 to perform the desired frequency to voltage conversion function. In the illustrated embodiment, resistor 142 is a 20k ohm potentiometer, and resistors 143–145 have values of 100k ohms, 2.28k ohms and 100k ohms, respectively.

Capacitors 148 and 149 preferably have values of 0.047 microfarads, respectively.

The output of F/V converter 140 is coupled to amplifier stage 48 which includes a filter for removing the ripple carried on the continuous DC signal from F/V converter 140 and a low pass filter. The output from F/V converter 140 splits into two paths which are both input into op amp 150. Through one path, F/V converter 140 is coupled to the non-inverting input of op amp 150 through the voltage divider of resistors 152-154. Through the other path, converter 140 is coupled to the inverting input of op amp 150 through capacitors 156 and 158 and the voltage divider of resistors 160 and 162. The presence of capacitors 156 and 158 in the one path produces a phase difference between the two paths which effectively cancels out the ripple component.

The gain of op amp 150 is determined by the 10k ohm feedback resistor 164. Resistors 152 is a 10k ohm potentiometer and resistors 153, 154, 160, and 162 preferably have values of 4.7k ohms, 10k ohms, 4.7k ohms, and 10k ohms, respectively. Capacitors 156 and 158 are each preferably 0.47 microfarads.

The output of op amp 150 is coupled to the inverting input of op amp 166 through 10k ohm resistor 168. The frequency response of op amp 166 is determined by resistors 170 and 172 and by capacitor 174, which preferably have values of 20k ohms (potentiometer), 910 ohms, and 20 microfarads, respectively. The non-inverting terminal of op amp 166 is coupled through 4.7k ohm resistor 175 to ground in order to eliminate drift of the DC offset voltage. Resistors 176 and 178 provide for the adjustment of the DC offset level of op amp 166, and resistors 180 and 182 provide for scaling of the output of op amp 166 so that the present invention is compatible with a large variety of recording devices. In the preferred embodiment, resistor 176 is a 20k ohm potentiometer and resistors 178, 180, and 182 preferably have values of 10k ohms, 499k ohms, and 500 ohms, respectively.

To provide a pair of reference signals for calibration purposes, strip chart calibration stage 52 derives a 48 Hz and a 54 Hz signal from a half wave rectified line signal. The half wave rectified line signal is derived by conventional methods from a line source and is input through an 8 microfarad coupling capacitor 184 and 22k ohm resistor 185 to a squaring circuit which includes a high gain op amp 186.

Diode 188 clamps the input voltage between approximately ground potential and negative three-fourths of a volt. Diode 190 provides a very high positive gain (approximately equal to the open loop gain of op amp 186) but eliminates the negative gain of the op amp such that the output is clamped between ground potential and plus five volts. The non-inverting input of op amp 186 is coupled to ground through 13k ohm resistor 192 to eliminate drift in the DC offset level. The output of op amp 186 is a square wave which has a frequency of 60 Hz.

The output of op amp 186 is coupled to a divide-by ten counter 194 which divides the frequency of the signal at its input down by a factor of ten such that the frequency of the signal in its output is 6 Hz. Counter 194 may be an RCA CD4018 CMOS integrated circuit.

The output of counter 194 is coupled to a phase locked loop (hereinafter referred to as "PLL") integrated circuit 196 which, in combination with counter 198 and Schmitt trigger 200, multiplies the signal on the input of PLL integrated circuit 196 by 8 or 9 depending on the position of calibration switch 56. PLL 196 may be a CD4046, counter 198 may be a CD4018, and Schmitt trigger 200 may be a CD4093—all of which are CMOS integrated circuits manufactured by RCA.

The configuration of PLL integrated circuit 196, counter 198, and Schmitt trigger 200 (along with resistors 201-204 and capacitor 206 and 208) is provided as specified by the RCA CMOS Applications Manual so as to perform a multiplication function which multiplies by a factor of 8 or 9 the frequency of the signal at the input of PLL integrated circuit 196. In the preferred embodiment, resistors 201-204 and capacitors 206 and 208 have values of 300k ohms, 150k ohms, 270k ohms, 330k ohms, 0.22 microfarads and 0.47 microfarads, respectively.

The output of PLL integrated circuit 196 is coupled through an 8 microfarad coupling capacitor 210 and a 22k ohm resistor 212 to op amp 214. The non-inverting input of op amp 214 is coupled through 13k ohm resistor 216 to ground, and the output of op amp 214 is coupled to strip chart calibration switch 56.

Calibration switch 56 is a double pole, triple throw switch. One pole 56a of switch 56 controls PLL 196, counter 198, and Schmitt trigger 200. The other pole 56b couples either the output from duty cycle modification stage 44 or the output from strip chart calibration stage 52 to F/V conversion stage 46.

When switch 56 is positioned as illustrated in FIG. 4, the output from duty cycle modification stage 44 is coupled to the F/V conversion stage 46, and the output signal from amplifier stage 48 is proportional to the frequency of vibration as detected by the sensing and transmitting circuit illustrated in FIG. 3. In addition, pole 56a of switch 56 disables PLL 196, counter 198 and Schmitt trigger 200 by pulling line 218 down to ground potential.

If, however, switch 56 is moved to one of the other positions, the output of calibration stage 52 is coupled to the F/V conversion stage 46 through pole 56b, and the output of amplifier stage 48 will be proportional to a 48 Hz or a 54 Hz signal depending on the particular position of switch 56. If, for example, switch 56 is switched to the position counterclockwise from the position illustrated in FIG. 4, pole 56a sets the configuration of PLL integrated circuit 196, counter 198, and Schmitt trigger 200 such that the output from divide by ten counter 194 is multiplied by 8, and a 48 Hz signal is coupled to the F/V conversion stage 46 through pole 56b. It will be apparent that if switch 56 were placed in the other position, a signal of 54 Hz would be coupled to F/V conversion stage 44. Power for each of the active devices described above is supplied by power supply stage 54. Power supply stage 54 includes conventional and well-known circuitry for deriving +5 Vdc from a conventional line source, and will not be discussed in detail herein.

Each of the monostable multivibrators described in FIGS. 3 and 4 may be provided by RCA CD4098 CMOS integrated circuits or by Fairchild 4528 CMOS integrated circuits. Each of the astable multivibrators may be provided by RCA CD4047 CMOS integrated circuits, and each of the op amps may be provided by Texas Instruments TL082 integrated circuits.

It will be apparent to one skilled in the art that modifications can be made to the circuits described above without departing from the essential characteristics of the present invention as set forth in the claims. Component values and the specific components identified above are given by way of example only and pertain only to one presently preferred embodiment.

The invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for measuring concentrations of supercooled liquid water in an atmosphere comprising:
a wire which is fixed at one end and free at the other end for collecting supercooled liquid water, said wire and collected supercooled water having a natural frequency which decreases in relation to an increase in mass of supercooled water collected on the wire, the mass of the supercooled water collected on the wire being substantially proportional to the concentration of supercooled liquid water in the surrounding atmosphere;
means for vibrating the wire; and
means for sensing the natural frequency of the wire in combination with the mass of the collected supercooled water.

2. An apparatus for measuring concentrations of supercooled liquid water as defined in claim 1 wherein at least a portion of the wire at the free end is magnetized and at least a portion of the wire at the free end is exposed to the atmosphere.

3. An apparatus for measuring concentrations of supercooled liquid water as defined in claim 2 further comprising an electronic circuit coupled between the sensing means and the vibrating means for controlling the vibrating means so as to vibrate the wire at a frequency which substantially corresponds to the natural frequency of the wire and collected supercooled water.

4. An apparatus for measuring concentrations of supercooled liquid water as defined in claim 3 wherein the sensing means comprises a sensing coil comprising a multi-turn wire coil positioned in close proximity to the magnetized portion of the wire such that movement of the wire induces a time varying curring in the sensing coil having a frequency which substantially corresponds to the natural frequency of the vibrating wire and the collected supercooled water.

5. An apparatus for measuring concentrations of supercooled liquid water as defined in claim 4 wherein the vibrating means comprises:
a driving coil comprising a multi-turn wire coil placed in close proximity to the wire; and
an electronic driving circuit electrically coupled to the electronic circuit for selectively supplying an alternating current to the driving coil so as to produce a magnetic flux around the wire, thereby initiating vibration of the wire.

6. An apparatus for measuring concentrations of supercooled liquid water as defined in claim 5 wherein the sensing means further comprises means for amplifying the current induced in the sensing coil, said amplifying means being electrically coupled to the driving coil, and the apparatus further including means for enabling the sensing means whenever the amplified current is above a predetermined threshold amplitude.

7. An apparatus for measuring concentrations of supercooled liquid water as defined in claim 3 further comprising:
means for deriving a continuous output signal proportional to the natural frequency of the wire and collected supercooled water, said deriving means coupled to the vibrating means; and
means for recording the continuous output signal.

8. An apparatus for measuring concentrations of supercooled liquid water as defined in claim 3 further comprising:
means for deriving a continuous output signal proportional to the natural frequency of the wire and collected supercooled water, said deriving means coupled to the vibrating means;
means for modulating the continuous output signal;
means for transmitting the modulated signal;
means for receiving the transmitted signal;
means for demodulating the received signal; and
means for recording the demodulated signal.

9. An apparatus for measuring concentrations of supercooled liquid water as defined in claim 1 wherein the apparatus is capable of collecting concentrations of supercooled water on the wire while traveling at speeds up to balloon velocities, the apparatus further being capable of determining the natural frequency of the wire and collected supercooled water at said speeds.

10. An apparatus for measuring concentrations of supercooled liquid water comprising:
a wire fixed at one end and free at the other end, said wire having at least a portion of the wire at the free end magnetized and having at least a portion of the wire at the free end exposed to the atmosphere so as to collect supercooled liquid water, said wire and collected supercooled water having a natural frequency related to the amount of supercooled water collected on the wire, the amount of supercooled water collected on the wire being substantially proportional to the concentration of supercooled liquid water;
a first multi-turn wire coil positioned in close proximity to the wire;
a first electronic circuit for selectively supplying an alternating current to the first wire coil;
a second multi-turn wire coil positioned in close proximity to the magnetized portion of the wire such that movement of the wire relative to the second wire coil induces a time varying current in the second wire coil;
a second electronic circuit electrically coupled to the second wire coil for amplifying the induced current;
means for enabling the first electronic circuit whenever the amplified current is above a predetermined threshold amplitude;
a third electronic circuit electrically coupled to the first wire coil for deriving a frequency modulated output signal having a signal frequency that substantially corresponds to the natural frequency;
a fourth electronic circuit for transmitting the modulated signal;
a fifth electronic circuit for receiving the transmitted signal;
a sixth electronic circuit for deriving a continuous output signal which is substantially proportional to the natural frequency; and
a continuous recording device for recording the continuous output signal.

11. An apparatus for measuring concentrations of supercooled liquid water as defined in claim 10 wherein the apparatus is capable of collecting concentrations of supercooled water on the wire while traveling at speeds up to balloon velocities, the apparatus further being capable of determining the natural frequency of the wire and collected supercooled water at said speeds.

12. A method for measuring supercooled liquid water concentration comprising the steps of:
   exposing a portion of a wire which is fixed at one end and free at the other end to the atmosphere so as to collect supercooled liquid water upon the wire through contact freezing, the wire and collected supercooled water having a natural frequency which decreases in relation to an increase in the mass of supercooled liquid water upon the wire;
   vibrating the wire;
   controlling the frequency of wire vibration such that said frequency substantially corresponds to the natural frequency of the wire in combination with the mass of the collected supercooled water; and
   measuring change in the natural frequency.

13. A method for measuring supercooled liquid water concentration as defined in claim 12 wherein the step of exposing a portion of wire to the atmosphere comprises placing a wire in the humidity duct of a balloon-borne radiosonde.

14. A method for measuring supercooled liquid water concentration as defined in claim 12 wherein the step of vibrating the wire comprises:
   positioning a first multi-turn wire coil in close proximity to the wire; and
   passing an alternating current through the wire coil so as to produce a time varying magnetic field around the wire.

15. A method for measuring supercooled liquid water concentration as defined in claim 12 wherein the step of controlling the frequency of wire vibration comprises:
   positioning a first multi-turn wire coil in close proximity to the wire, with at least a portion of the wire being magnetized;
   positioning a second multi-turn wire coil in close proximity to the magnetized portion of the wire such that movement of the wire relative to the second wire coil induces a time varying current in the second wire coil, said time varying current having a frequency that substantially corresponds to the natural frequency of the wire and the collected supercooled water;
   amplifying the induced current; and
   feeding the amplified current back to the first wire coil so as to produce a time varying magnetic field around the wire, said time varying magnetic field having a frequency that substantially corresponds to the natural frequency of the wire and the collected supercooled water.

16. A method for measuring supercooled liquid water concentration as defined in claim 12 wherein the step of measuring change in natural frequency comprises:
   deriving a continuous output signal proportional to the natural frequency; and
   recording the continuous output signal.

17. A method for measuring supercooled liquid water concentration as defined in claim 12 wherein the step of exposing a portion of a wire to the atmosphere further comprises the step of collecting supercooled liquid water upon the wire while said wire is traveling through the atmosphere at speeds up to balloon velocities.

18. A method for measuring supercooled liquid water concentrations as defined in claim 12 wherein at least a portion of the wire is magnetized.

19. A method for measuring supercooled liquid water concentration in an atmosphere comprising the steps of:
   exposing a portion of a wire which is fixed at one end and free at the other end to the atmosphere so as to collect supercooled liquid water upon the wire through contact freezing, at least a portion of the wire being magnetized;
   positioning a first multi-turn wire coil in close proximity to the wire;
   passing an alternating current through the first wire coil;
   positioning a second multi-turn wire coil in close proximity to the magnetized portion of the wire such that movement of the wire relative to the second wire coil induces a time varying current in the second wire coil;
   amplifying the induced current;
   feeding the amplified current back to the first wire coil;
   deriving a continuous output signal from the first wire coil; and
   recording the continuous output signal.

20. A method for measuring supercooled liquid water concentration in an atmosphere as defined in claim 19 wherein the step of exposing a portion of a wire to the atmosphere further comprises the step of collecting supercooled liquid water upon the wire while said wire is traveling through the atmosphere at speeds up to balloon velocities.

* * * * *

UNITED STATES PATENT AND TRADEMARK OFFICE
CERTIFICATE OF CORRECTION

PATENT NO. : 4,441,363
DATED : April 10, 1984
INVENTOR(S) : Geoffrey E. Hill, et al.

It is certified that error appears in the above-identified patent and that said Letters Patent is hereby corrected as shown below:

Column 5, lines 36-39 (in Equation 2) should read as follows:

$$\frac{\int_0^{L_1} [(E_1 I_1)/2](\partial^2 y/\partial x^2)^2 dx + \int_{L_1}^{L} [(E_2 I_2)/2](\partial^2 y/\partial x^2)^2 dx}{\omega^{-2} \int_0^{L_1} [M_1/2](\partial y/\partial t)^2 dx + \omega^{-2} \int_{L_1}^{L} [M_2/2](\partial y/\partial t)^2 dx}, \quad (2)$$

Column 5, lines 64-68 (in Equations 6 and 7); every occurrence of "y" should be --$\bar{y}$--

Column 11, line 30, "stage" should be --state--

Column 15, line 47 (claim 4), "curring" should be --current--

*Signed and Sealed this*

Sixth Day of November 1984

[SEAL]

*Attest:*

GERALD J. MOSSINGHOFF

*Attesting Officer*     *Commissioner of Patents and Trademarks*